(12) United States Patent
Kuribayashi et al.

(10) Patent No.: US 11,976,204 B2
(45) Date of Patent: May 7, 2024

(54) COMPOSITION FOR AQUEOUS INK JET

(71) Applicant: Seiko Epson Corporation, Tokyo (JP)

(72) Inventors: Homare Kuribayashi, Ikeda (JP); Shotaro Watanabe, Suwa (JP); Kei Hiruma, Chino (JP); Masato Hanamura, Shiojiri (JP); Koji Imamura, Shiojiri (JP); Jungo Asano, Shiojiri (JP)

(73) Assignee: SEIKO EPSON CORPORATION (JP)

( * ) Notice: Subject to any disclaimer, the term of this patent is extended or adjusted under 35 U.S.C. 154(b) by 856 days.

(21) Appl. No.: 17/042,077

(22) PCT Filed: Feb. 6, 2019

(86) PCT No.: PCT/JP2019/004127
§ 371 (c)(1),
(2) Date: Sep. 25, 2020

(87) PCT Pub. No.: WO2019/187657
PCT Pub. Date: Oct. 3, 2019

(65) Prior Publication Data
US 2021/0139722 A1 May 13, 2021

(30) Foreign Application Priority Data

Mar. 28, 2018 (JP) .................. 2018-061328

(51) Int. Cl.
*C09D 11/328* (2014.01)
*C08K 5/42* (2006.01)
*C09D 11/38* (2014.01)

(52) U.S. Cl.
CPC .............. *C09D 11/328* (2013.01); *C08K 5/42* (2013.01); *C09D 11/38* (2013.01)

(58) Field of Classification Search
CPC ........ C09D 11/328; C09D 11/38; C08K 5/42; B41J 2/01; B41M 5/00; C07C 309/50; C09B 45/16; C09B 45/22; D06P 5/30
See application file for complete search history.

(56) References Cited

U.S. PATENT DOCUMENTS

| 5,017,227 | A | * | 5/1991 | Koike | ................. | C09D 11/328 347/100 |
| 2009/0165669 | A1 | * | 7/2009 | Iwamura | ............. | C09D 11/328 106/31.13 |

FOREIGN PATENT DOCUMENTS

JP  2002256187 A     9/2002
JP  2017110096 A  *  6/2017

OTHER PUBLICATIONS

"Acid Red 27." ChemicalBook, www.chemicalbook.com/ChemicalProductProperty_EN_CB2468655.htm. Accessed May 12, 2023. (Year: 2023).*

(Continued)

*Primary Examiner* — Jennifer A Smith
*Assistant Examiner* — Jeffrey Eugene Barzach
(74) *Attorney, Agent, or Firm* — Harness, Dickey & Pierce, P.L.C.

(57) ABSTRACT

A composition for aqueous ink jet contains a specific dye which is one or more coloring materials selected from the group consisting of C. I. Acid Black 172 and C. I. Acid Black 194, and a specific aromatic compound which is at least one compound selected from the group consisting of compounds represented by formulae (1) to (4) below. The content of the specific aromatic compound relative to 100 parts by mass of the specific dye is 0.2 parts by mass or more and 50 parts by mass or less.

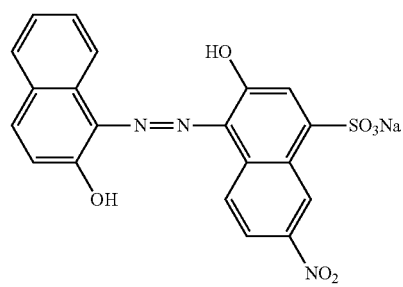

(1)

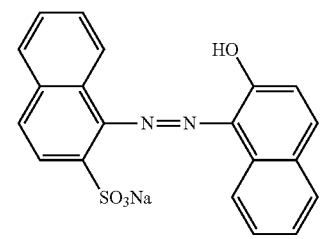

(2)

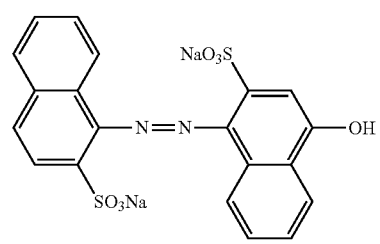

(3)

(Continued)

-continued

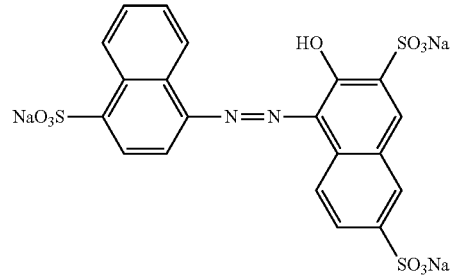

(4)

4 Claims, No Drawings

(56) References Cited

OTHER PUBLICATIONS

English Machine Translation of JP2017110096A ("Machine_Translation_Takeda_JP_2017110096_A") (Year: 2017).*
International Search Report issued in PCT/JP2019/004127 (in English and Japanese), dated Mar. 26, 2019; ISA/JP.

* cited by examiner

COMPOSITION FOR AQUEOUS INK JET

CROSS REFERENCE TO RELATED APPLICATIONS

This application is a U.S. National Phase application of International Application No. PCT/JP2019/004127, filed on Feb. 6, 2019 which claims priority to Japanese Patent Application No. 2018-061328, filed on Mar. 28, 2018. The entire disclosures of the above applications are expressly incorporated by reference herein.

BACKGROUND

Technical Field

The present invention relates to a composition for aqueous ink jet.

Related Art

In recent years, the use of ink jet printing has been expanded, and ink jet printing has been applied to office/home printing machines and also applied to commercial printing, textile printing, and the like.

In addition, an ink for ink jet (composition for ink jet) containing a dye has also been used.

An ink for ink jet is required to have excellent stability (ejection stability) of ejection by an ink jet method for forming a desired pattern.

In order to improve the ejection stability of an ink for ink jet, an ink for ink jet containing a polyoxyethylene alkyl ether acetic acid salt-based surfactant is proposed (refer to Japanese Unexamined Patent Application Publication No. 2002-256187).

However, when a polyoxyethylene alkyl ether acetic acid salt-based surfactant is used in combination with a predetermined type of coloring agent (particularly, a self-dispersed pigment), an excellent effect is obtained, but not all coloring agents provide the effect of improving ejection stability. In particular, C. I. Acid Black 172 and C. I. Acid Black 194 have the characteristics of excellent color development etc. However, the use in combination with the polyoxyethylene alkyl ether acetic acid salt-based surfactant exhibits the unsatisfactory effect of improving ejection stability.

SUMMARY

The present invention has been achieved for solving the problem described above, and can be realized as the following application examples.

[1] A composition for aqueous ink jet containing a specific dye which is one or more coloring materials selected from the group consisting of C. I. Acid Black 172 and C. I. Acid Black 194, and a specific aromatic compound which is at least one compound selected from the group consisting of a compound represented by formula (1) below, a compound represented by formula (2) below, a compound represented by formula (3) below, and a compound represented by formula (4) below, the content of the specific aromatic compound relative to 100 parts by mass of the specific dye being 0.2 parts by mass or more and 50 parts by mass or less.

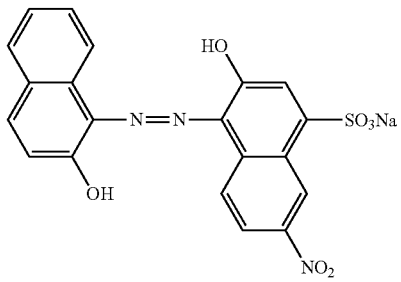

(1)

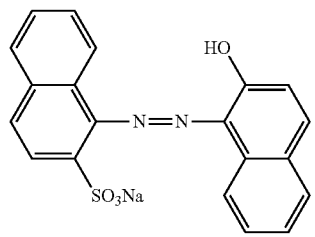

(2)

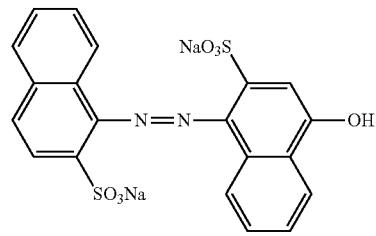

(3)

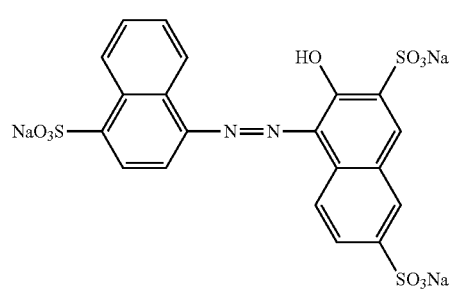

(4)

[2] The composition for aqueous ink jet described above in [1], wherein the content of the specific aromatic compound in the composition for aqueous ink jet is 0.02% by mass or more and 5.0% by mass or less.

[3] The composition for aqueous ink jet described above in [1] or [2], wherein the content of the specific dye in the composition for aqueous ink jet is 5.0% by mass or more and 15% by mass or less.

[4] The composition for aqueous ink jet described above in any one of [1] to [3], wherein the viscosity at 25° C. is 2 mPa·s or more and 30 mPa·s or less.

DETAILED DESCRIPTION

Preferred embodiments of the present invention are described in detail below.

Composition for Aqueous Ink Jet

Among various dyes (particularly, acid dyes), C. I. Acid Black 172 and C. I. Acid Black 194 have the characteristics such as excellent color development etc., but have the following problem. That is, when C. I. Acid Black 172 and C. I. Acid Black 194 are used as constituent components of a composition for aqueous ink jet, there is a problem that ejection by an ink jet method cannot be stably performed due to the precipitation of the dyes near nozzles.

Therefore, the inventor of the present invention has earnestly investigated for the purpose of providing a composition for aqueous ink jet which can effectively prevent the occurrence of the problem described above while utilizing the excellent characteristics possessed by C. I. Acid Black 172 and C. I. Acid Black 194.

As a result, the present invention has been achieved.

That is, a composition for aqueous ink jet of the present invention includes a specific dye which is one or more coloring materials selected from the group consisting of C. I. Acid Black 172 and C. I. Acid Black 194, and a specific aromatic compound which is at least one compound selected from the group consisting of a compound represented by formula (1) below, a compound represented by formula (2) below, a compound represented by formula (3) below, and a compound represented by formula (4) below, the content of the specific aromatic compound relative to 100 parts by mass of the specific dye being 0.2 parts by mass or more and 50 parts by mass or less.

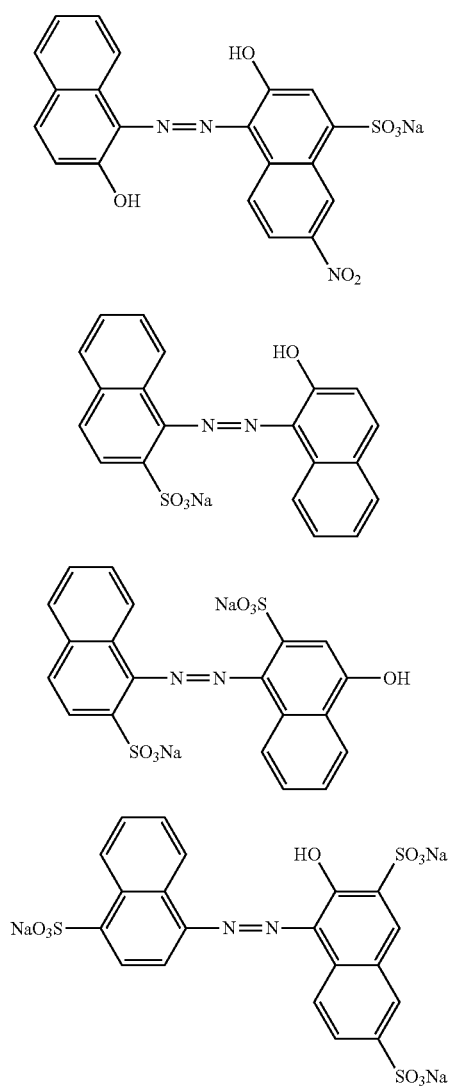

This configuration can provide a composition for aqueous ink jet which enables stable ejection by an ink jet method while utilizing the characteristics of C. I. Acid Black 172 and C. I. Acid Black 194.

More specifically, the solubility and dissolution stability of the specific dye can be improved by containing a predetermined ratio of the specific aromatic compound together with the specific dye. Consequently, clogging of a head filter, nozzles, or the like can be effectively prevented from occurring due to the unintended precipitation of the specific dye. In particular, it is possible to improve intermittent ejection characteristics and to improve ejection stability (recovery property) after recovery from pausing of an apparatus (printer) which performs ejection by an ink jet method. This can lengthen the flashing distance and can contribute to further improvement in the printing speed.

While, when the configuration described above in not satisfied, a satisfactory effect cannot be obtained.

For example, when at least one (specific dye) of C. I. Acid Black 172 and C. I. Acid Black 194 is not contained as a dye, satisfactory coloring development cannot be obtained.

In addition, when compounds (specific aromatic compounds) represented by the formula (1) to the formula (4) are not contained, precipitation of the specific dyes (C. I. Acid Black 172 and C. I. Acid Black 194) near nozzles cannot be preferably prevented, thereby destabilizing ejection by an ink jet method.

Also, even when the compounds (specific aromatic compounds) represented by the formula (1) to the formula (4) are contained, with an excessively low content, precipitation of the specific dye cannot be preferably prevented, thereby destabilizing ejection by an ink jet method.

The excessively high content of the compounds (specific aromatic compounds) represented by the formula (1) to the formula (4) increases the viscosity of the composition for aqueous ink jet and thus also makes impossible stable ejection by an ink jet method. In addition, election stability (recovery property) after recovery from pausing tends to be impaired.

Specific Dye

The composition for aqueous ink jet of the present invention contains, as a dye, the specific dye which is one or more coloring materials selected from the group consisting of C. I. Acid Black 172 and C. I. Acid Black 194.

As described above, such a specific dye has the characteristic of excellent color development.

The content of the specific dye in the composition for aqueous ink jet is not particularly limited but is preferably 5.0% by mass or more and 15% by mass or less, more preferably 6.0% by mass or more and 14% by mass or less, and still more preferably 7.0% by mass or more and 13% by mass or less.

Thus, a higher color density can be obtained in a recorded portion formed by using the composition for aqueous ink jet, and the ejection stability and storage stability of the composition for aqueous ink jet can be further improved.

Specific Aromatic Compound

The composition for aqueous ink jet of the present invention contains the specific aromatic compound as at least one compound selected from the group consisting of a compound represented by the formula (1) above, a compound represented by the formula (2) above, a compound represented by the formula (3) above, and a compound represented by the formula (4) above.

This specific aromatic compound has the very small adverse effect on a color or the like of the composition for aqueous ink jet and of a recorded portion (print portion)

formed by the composition for aqueous ink jet, while the compound has the function of improving the solubility and dissolution stability of the specific dye.

Among the four compounds, the compound represented by the formula (1) is particularly preferably contained as the specific aromatic compound.

Thus, the effect as described above can be more remarkably exhibited.

The ratio of the compound represented by the formula (1) to the whole of the specific aromatic compound contained in the composition for aqueous ink jet is preferably 10% by mass or more and 100% by mass or less, more preferably 20% by mass or more and 100% by mass or less, and still more preferably 30% by mass or more and 100% by mass or less.

Thus, the effect as described above can be more remarkably exhibited.

As described above, the content of the specific aromatic compound relative to 100 parts by mass of the specific dye may be 0.2 parts by mass or more and 50 parts by mass or less, is preferably 0.3 parts by mass or more 30 parts by mass or less, more preferably 0.4 parts by mass or more and 10 parts by mass or less, and still more preferably 0.5 parts by mass or more and 5.0 parts by mass or less.

Thus, the effect by containing the specific aromatic compound described above is more remarkably exhibited while effectively preventing an excessive increase in viscosity of the composition for aqueous ink jet.

The content of the specific aromatic compound in the composition for aqueous ink jet is preferably 0.02% by mass or more and 5.0% by mass or less, more preferably 0.03% by mass or more and 3.0% by mass or less, still more preferably 0.04% by mass or more and 2.0% by mass or less, and most preferably 0.05% by mass or more and 1.0% by mass or less.

Thus, the effect by containing the specific aromatic compound described above is more remarkably exhibited while effectively preventing an excessive increase in viscosity of the composition for aqueous ink jet.

Water

The composition for aqueous ink jet contains water.

The content of water in the composition for aqueous ink jet is not particularly limited, but is preferably 30% by mass or more and 85% by mass or less, more preferably 35% by mass or more and 80% by mass or less, and still more preferably 40% by mass or more and 75% by mass or less.

Thus, the viscosity of the composition for aqueous ink jet can be more securely adjusted to a preferred value, and ejection stability by an ink jet method can be more improved.

Solvent Other than Water

The composition for aqueous ink jet may contain a solvent other than water.

Thus, for example, the viscosity of the composition for aqueous ink jet can be preferably adjusted, and moisture retention of the composition for aqueous ink jet can be enhanced. Consequently, droplets can be more stably ejected by an ink jet method.

The solvent other than water is in a simple liquid form (liquid) at room temperature (25° C.) and preferably has a boiling point (boiling point under 1 atm or less) of 180° C. or more and 320° C. or less, more preferably 185° C. or more and 310° C. or less, and still more preferably 190° C. or more and 300° C. or less.

Examples of the solvent other than water contained in the composition for aqueous ink jet include alkylene glycol and ethers and esters thereof (also generally referred to as "alkylene glycols" hereinafter); tri- or higher polyhydric alcohols; nitrogen-containing heterocyclic compounds; lactones such as γ-butyrolactone and the like; and the like.

More specific examples of the alkylene glycols include 1,2-butanediol, 1,2-heptanediol, 1,2-hexanediol, 1,2-heptanediol, 1,2-propanediol (propylene glycol), 1,3-propanediol, 1,3-butanediol, 1,4-butanediol, 1,5-heptanediol, 1,6-hexanediol, 2-ethyl-2-methyl-1,3-propanediol, 2-methyl-2-propyl-1,3-propanediol, 2-methyl-1,3-propanediol, 2,2-dimethyl-1,3-propanediol, 3-methyl-1,3-butanediol, 2-ethyl-1,3-hexanediol, 3-methyl-1,5-pentanediol, 2-methylpentane-2,4-diol, triethylene glycol monomethyl ether, triethylene glycol monobutyl ether, diethylene glycol monomethyl ether, diethylene glycol monobutyl ether, diethylene glycol, dipropylene glycol, triethylene glycol, and the like.

The tri- or higher polyhydric alcohols is, for example, glycerin.

Examples of the nitrogen-containing heterocyclic compounds include N-methyl-2-pyrrolidone, N-ethyl-2-pyrrolidone, N-vinyl-2-pyrrolidone, 2-pyrrolidone, 5-methyl-2-pyrrolidone, and the like.

The composition for aqueous ink jet may contain one component or a plurality of components as the solvent other than water.

The content of the solvent other than water in the composition for aqueous ink jet is preferably 1% by mass or more and 40% by mass or less, more preferably 5% by mass or more and 35% by mass or less, and still more preferably 10% by mass or more and 30% by mass or less.

Thus, the effect by containing the solvent other than water is more remarkably exhibited.

Urea

The composition for aqueous ink jet may contain urea.

The urea functions as a moisturizer of the composition for aqueous ink jet and also functions as a dyeing auxiliary for improving the dyeing property of a dye.

Examples of the urea include urea, ethylene urea, tetramethyl urea, thiourea, 1,3-dimethyl-2-imidazolidinone, and the like.

The content of the urea in the composition for aqueous ink jet is preferably 0.5% by mass or more and 15% by mass or less, more preferably 1.0% by mass or more and 12% by mass or less, and still more preferably 2.0% by mass or more and 10% by mass or less.

Thus, the contents of the specific dye and the specific aromatic compound can be prevented from being decreased, and the effect by containing the urea as described above can be more remarkably exhibited while satisfactorily exhibiting the functions.

Surfactant

The composition for aqueous ink jet may contain a surfactant.

Thus, the wettability of a recording medium (substrate) with the composition for aqueous ink jet can be more improved, thereby causing an advantage for producing better image quality.

Usable examples of the surfactant contained in the composition for aqueous ink jet include various surfactants such as an anionic surfactant, a cationic surfactant, a nonionic surfactant, and the like.

More specific examples of the surfactant contained in the composition for aqueous ink jet include an acetylene-based surfactant, a silicone-based surfactant, a fluorine-based surfactant, and the like.

The content of the surfactant in the composition for aqueous ink jet is preferably 0.2% by mass or more and 4.0% by mass or less, more preferably 0.3% by mass or more and 3.5% by mass or less, and still more preferably 0.5% by mass or more and 3.0% by mass or less.

Thus, the contents of the specific dye and the specific aromatic compound can be prevented from being decreased, and the effect by containing the surfactant as described above can be more remarkably exhibited while satisfactorily exhibiting the function.

Other Component

The composition for aqueous ink jet may contain a component other the components described above.

Examples of the other component include coloring agents other than C. I. Acid Black 172 and C. I. Acid Black 194; pH adjusters such as tripropanolamine (TPA), triethanolamine (TEA), N,N-bis(2-hydroxyethyl)-2-aminoethanesuofonic acid (BES), 3-[4-(2-hydroxyethyl)-1-piperazinyl]propanesulfonic acid (EPPS), 2-morpholinoethanesulfonic acid (MES), piperazine-N,N'-bis(2-hydroxypropanesulfonic acid) (POPSO), and the like; chelating agents such as ethylenediaminetetraacetic acid salts (EDTA) and the like; antiseptic agents/antifungal agents such as sodium benzoate, pentachlorophenol sodium, 2-pyridinethiol-1-oxide sodium, sodium sorbate, sodium dehydroacetate, 1,2-dibenzoisothiazolin-3-one, 4-chloro-3-methylphenol, and the like; anti-rusting agents such as benzotriazole and the like; an anti-oxidant; an ultraviolet absorber; an oxygen absorber; a dissolving aid; and the like.

The content (total content when a plurality of components are contained as the other component) of the other component is preferably 5% by mass or less and more preferably 3% by mass or less.

The viscosity at 25° C. of the composition for aqueous ink jet is preferably 2 mPa·s or more and 30 mPa·s or less, more preferably 3 mPa·s or more and 20 mPa·s or less, and still more preferably 4 mPa·s or more and 10 mPa·s or less.

Thus, the ejection stability of the composition for aqueous ink jet is more improved.

The viscosity can be determined by measurement using a Cannon-Fenske viscometer.

The composition for aqueous ink jet of the present invention is applied, in the state of being housed in a vessel such as a cartridge, a bag, a tank, or the like, to a recording apparatus using an ink jet method. In other words, a recording apparatus according to the present invention is provided with a vessel (ink cartridge or the like) which houses the composition for aqueous ink jet of the present invention.

Recording Medium

Examples of a recording medium to which the composition for aqueous ink jet of the present invention is applied include, but are not particularly limited to, fabrics (hydrophobic fiber fabrics and the like), resin (plastic) films, paper, glass, metals, porcelains, and the like. Also, besides a sheet shape, a material having a three-dimensional shape, for example, a spherical shape, a rectangular parallelepiped shape, or the like, may be used as the recording medium.

When the recording medium is a fabric, examples of the fibers constituting the fabric include polyester fibers, nylon fibers, triacetate fibers, diacetate fibers, polyamide fibers, a blend of two or more types of these fibers, and the like. There may also be used a blend of these fibers with regenerated fibers of rayon or the like or with natural fibers of cotton, silk, wool, or the like may be used.

When the recording medium is a resin (plastic) film, examples of the resin (plastic) film include a polyester film, a polyurethane film, a polycarbonate film, a polyphenylene sulfide film, a polyimide film, a polyamide-imide film, and the like.

The resin (plastic) film may be a laminate formed by laminating a plurality of layers or may be composed of a graded material whose composition is changed in a graded manner.

Recording Method (Method for Producing Recorded Product)

A recorded product can be obtained by, for example, general ink jet printing (for example, direct printing) using the composition for aqueous ink jet.

Described below is a recording method (method for producing a recorded product) according to a preferred embodiment using the composition for aqueous ink jet of the present invention.

The recording method (method for producing a recorded product) according to the present embodiment includes a pretreatment step of pre-treating a fabric used as a recording medium, a composition adhering step of adhering the composition for aqueous ink jet ejected by an ink jet method to the pre-treated fabric, a fixing step of fixing an image formed by the composition for aqueous ink jet to the fabric (recording medium), and a washing step of washing the fabric (recording medium) to which the image has been fixed.

A known method and operation can be used in each of the steps, but the specific form of each of the steps is described below.

Pretreatment Step

In the present embodiment, the fabric used as the recording medium is pre-treated in advance before the composition for aqueous ink jet of the present invention is adhered to the fabric used as the recording medium.

The pretreatment can use, for example, a known pretreatment agent, and the pretreatment agent generally contains a sizing agent, a pH adjuster, and a hydrotropic agent.

Preferred usable examples of the sizing agent include natural gums such as guar, locust bean, and the like; starches; sodium alginate; seaweeds such as Funori and the like; plant skin materials such as pectic acid and the like; cellulose derivatives such as methyl cellulose, ethyl cellulose, hydroxyethyl cellulose, carboxymethyl cellulose, and the like; processed starches such as roasted starch, alpha-starch, carboxymethyl starch, carboxyethyl starch, hydroxyethyl starch, and the like; processed natural gums such as shiratsu gum, roast bean gum, and the like; synthetic paste such as algin derivatives, polyvinyl alcohol, polyacrylic acid esters, and the like; an emulsion, and the like.

Preferred usable examples of the pH adjuster include acid ammonium salts such as ammonium sulfate, ammonium tartrate, and the like; and the like.

Usable examples of the hydrotropic agent include various ureas such as urea, alkylureas such as dimethylurea, thiourea, monomethylthiourea, dimethylthiourea, and the like, and the like.

The pretreatment agent may further contain, for example, silica.

Composition Adhering Step

In the composition adhering step, the composition for aqueous ink jet of the present invention is ejected as droplets by an ink jet method, and the droplets are adhered to a fabric (pretreated fabric) used as a recording medium. Consequently, a desired image (pattern) is formed. The image may be formed by using a plurality of types of compositions for aqueous ink jet (for example, a plurality of types of compositions for aqueous ink jet having different compositions).

The ink jet method of ejecting the composition for aqueous ink jet may be of any type, and examples thereof include a charge deflection type, an on-demand type (a piezo type, a bubble jet (registered trademark) type, and the like), and the like. Among these, the piezo type is preferred from the viewpoint of high definition, miniaturization of an apparatus, etc.

Fixing Step

The fixing step is generally performed under a high-temperature humidified condition.

The treatment temperature in the fixing step is, for example, preferably 90° C. or more and 150° C. or less, more preferably 95° C. or more and 130° C. or less, and still more preferably 98° C. or more and 120° C. or less.

The treatment time in the fixing step is not particularly limited, but is preferably 5 minutes or more and 120 minutes or less, more preferably 10 minutes or more and 90 minutes or less, and still more preferably 15 minutes or more and 60 minutes or less.

The high-temperature humidifying treatment in the fixing step can use any one of various steamers (for example, steamer type "DHe" manufactured by Mathis AG).

Washing Step

The washing step is performed for the recording medium (recorded product) on which the image formed by the composition for aqueous ink jet has been fixed.

The washing step can be performed by, for example, rubbing/washing the recording medium, on which the image has been fixed, with tap water, and then immersing the recording medium under proper stirring in a washing solution prepared by adding a nonionic soaping agent to hot water of 40° C. or more and 70° C. or less. The immersion time in the washing solution can be set to, for example, 5 minutes or more and 60 minutes or less. Then, the washing agent is removed by hand-rubbing/washing while adding tap water to the solution.

The preferred embodiments of the present invention are described above, but the present invention is not limited to these embodiments.

EXAMPLES

Next, examples of the present invention are described.

[1] Preparation of Composition for Aqueous Ink Jet

Example 1

First, commercial C. I. Acid Black 172 was purified by activated carbon filtration, microfiltration, and ultrafiltration.

Then, the purified C. I. Acid Black 172 was mixed at a predetermined ratio with a compound represented by the formula (1), glycerin (Gly), diethylene glycol (DEG), triethylene glycol (TEG), triethylene glycol monobutyl ether (TEGmBE), 2-pyrrolidone (2-Py), Olfine E1010 (manufactured by Nissin Chemical Industry Co., Ltd.), triethanolamine serving as a pH adjuster, urea, benzotriazole serving as an anti-rusting agent, ethylenediamine tetraacetic acid salt (EDTA) serving as a chelating agent, PROXEL-XL2(S) (manufactured by Lonza Japan Ltd.) serving as an antifungal agent (antiseptic agent), and water, thereby preparing a composition for aqueous ink jet having a composition shown in Table 1.

Examples 2 to 12

Compositions for aqueous ink jet were produced by the same method as in Example 1 except that the types and ratios of the components mixed with C. I. Acid Black 172 purified as described above were changed to provide compositions shown in Table 1.

Example 13

First, commercial C. I. Acid Black 194 was purified by activated carbon filtration, microfiltration, and ultrafiltration.

Then, the purified C. I. Acid Black 194 was mixed at a predetermined ratio with a compound represented by the formula (1), glycerin (Gly), diethylene glycol (DEG), triethylene glycol (TEG), triethylene glycol monobutyl ether (TEGmBE), 2-pyrrolidone (2-Py), Olfine E1010 (manufactured by Nissin Chemical Industry Co., Ltd.), triethanolamine serving as a pH adjuster, urea, benzotriazole serving as an anti-rusting agent, ethylenediamine tetraacetic acid salt (EDTA) serving as a chelating agent, PROXEL-XL2(S) (manufactured by Lonza Japan Ltd.) serving as an antifungal agent (antiseptic agent), and water, thereby preparing a composition for aqueous ink jet having a composition shown in Table 1.

Examples 14 to 17

Compositions for aqueous ink jet were produced by the same method as in Example 13 except that the types and ratios of the components mixed with C. I. Acid Black 194 purified as described above were changed to provide compositions shown in Table 1 and Table 2.

Example 18

C. I. Acid Black 172 purified by the same method as in Example 1 and C. I. Acid Black 194 purified by the same method as in Example 13 were mixed at a predetermined ratio with a compound represented by the formula (1), a compound represented by the formula (2), a compound represented by the formula (3), a compound represented by the formula (4), glycerin (Gly), diethylene glycol (DEG), triethylene glycol (TEG), triethylene glycol monobutyl ether (TEGmBE), 2-pyrrolidone (2-Py), Olfine E1010 (manufactured by Nissin Chemical Industry Co., Ltd.), triethanolamine serving as a pH adjuster, urea, benzotriazole serving as an anti-rusting agent, ethylenediamine tetraacetic acid salt (EDTA) serving as a chelating agent, PROXEL-XL2(S) (manufactured by Lonza Japan Ltd.) serving as an antifungal agent (antiseptic agent), and water, thereby preparing a composition for aqueous ink jet having a composition shown in Table 1.

Comparative Examples 1 to 3

Compositions for aqueous ink jet were produced by the same method as in Example 1 except that the types and ratios of the components mixed with C. I. Acid Black 172 purified as described above were changed to provide compositions shown in Table 2.

Comparative Examples 4 and 5

Compositions for aqueous ink jet were produced by the same method as in Example 11 except that the types and ratios of the components mixed with C. I. Acid Black 194 purified as described above were changed to provide compositions shown in Table 2.

The composition etc. of the composition for aqueous ink jet of each of the examples and each of the comparative examples are shown in Table 1 and Table 2. In the tables, the purified product of C. I. Acid Black 172 is denoted by "AB172", the purified product of C. I. Acid Black 194 by "AB194", the compound represented by the formula (1) by "Formula (1)", the compound represented by the formula (2) by "Formula (2)", the compound represented by the formula (3) by "Formula (3)", the compound represented by the formula (4) by "Formula (4)", glycerin by "Gly", diethylene glycol by "DEG", triethylene glycol by "TEG", triethylene glycol monobutyl ether by "TEGmBE", 2-ethyl-1,3-hexanediol by "2E13HD", 2-pyrrolidone by "2-Py", Olfine E1010 (manufactured by Nissin Chemical Industry Co., Ltd.) by "E1010", triethanolamine by "TEA", benzotriazole by "BTA", ethylenediamine tetraacetic acid salt by "EDTA", PROXEL-XL2(S) (manufactured by Lonza Japan Ltd.) by "XL2", $C_{13}H_{27}O(C_2H_4O)_3CH_2COONa$ (manufactured by Nikko Chemicals Co., Ltd., ECTD3NEX) by "ECTD3NEX", and SAG30 (manufactured by Nippon Unica Co., Ltd.) by "SAG30". The viscosity (viscosity determined by measurement using a Cannon-Fenske viscometer) at 25° C. of the composition for aqueous ink jet of any one of the examples was a value within a range of 4 mPa·s or more and 10 mPa·s or less.

TABLE 1

|  |  | Example 1 | Example 2 | Example 3 | Example 4 | Example 5 | Example 6 | Example 7 | Example 8 |
|---|---|---|---|---|---|---|---|---|---|
| Content [parts by mass] | AB172 | 10.00 | 10.00 | 10.00 | 10.00 | 10.00 | 10.00 | 10.00 | 10.00 |
|  | AB194 | — | — | — | — | — | — | — | — |
|  | Formula (1) | 0.10 | 3.00 | 1.00 | 0.02 | 5.00 | — | — | — |
|  | Formula (2) | — | — | — | — | — | 0.10 | — | — |
|  | Formula (3) | — | — | — | — | — | — | 0.10 | — |
|  | Formula (4) | — | — | — | — | — | — | — | 0.10 |
|  | Gly | 3.00 | 3.00 | 3.00 | 3.00 | 3.00 | 3.00 | 3.00 | 3.00 |
|  | DEG | 1.00 | 1.00 | 1.00 | 1.00 | 1.00 | 1.00 | 1.00 | 1.00 |
|  | TEG | 1.00 | 1.00 | 1.00 | 1.00 | 1.00 | 1.00 | 1.00 | 1.00 |
|  | TEGmBE | 2.00 | 2.00 | 2.00 | 2.00 | 2.00 | 2.00 | 2.00 | 2.00 |
|  | 2E13HD | — | — | — | — | — | — | — | — |
|  | 2-Py | 10.00 | 10.00 | 10.00 | 10.00 | 10.00 | 10.00 | 10.00 | 10.00 |
|  | E1010 | 1.00 | 1.00 | 1.00 | 1.00 | 1.00 | 1.00 | 1.00 | 1.00 |
|  | TEA | 1.00 | 1.00 | 1.00 | 1.00 | 1.00 | 1.00 | 1.00 | 1.00 |
|  | Urea | 5.00 | 5.00 | 5.00 | 5.00 | 5.00 | 5.00 | 5.00 | 5.00 |
|  | BTA | 0.01 | 0.01 | 0.01 | 0.01 | 0.01 | 0.01 | 0.01 | 0.01 |
|  | EDTA | 0.02 | 0.02 | 0.02 | 0.02 | 0.02 | 0.02 | 0.02 | 0.02 |
|  | XL2 | 0.20 | 0.20 | 0.20 | 0.20 | 0.20 | 0.20 | 0.20 | 0.20 |
|  | ECTD3NEX | — | — | — | — | — | — | — | — |
|  | SAG30 | — | — | — | — | — | — | — | — |
|  | Water | 67.67 | 62.77 | 64.77 | 66.75 | 61.77 | 65.67 | 65.67 | 65.67 |
| Total |  | 102 | 100 | 100 | 101 | 101 | 100 | 100 | 100 |

|  |  | Example 9 | Example 10 | Example 11 | Example 12 | Example 13 | Example 14 | Example 15 |
|---|---|---|---|---|---|---|---|---|
| Content [parts by mass] | AB172 | 10.00 | 10.00 | 5.00 | 15.00 | — | — | — |
|  | AB194 | — | — | — | — | 10.00 | 10.00 | 10.00 |
|  | Formula (1) | 0.04 | 0.40 | 0.01 | 7.50 | 0.10 | 1.00 | 0.02 |
|  | Formula (2) | 0.01 | 0.10 | — | — | — | — | — |
|  | Formula (3) | 0.01 | 0.10 | — | — | — | — | — |
|  | Formula (4) | 0.01 | 0.10 | — | — | — | — | — |
|  | Gly | 3.00 | 3.00 | 3.00 | 3.00 | 3.00 | 3.00 | 3.00 |
|  | DEG | 1.00 | 1.00 | 1.00 | 1.00 | 1.00 | 1.00 | 1.00 |
|  | TEG | 1.00 | 1.00 | 1.00 | 1.00 | 1.00 | 1.00 | 1.00 |
|  | TEGmBE | 2.00 | 2.00 | 2.00 | 2.00 | 2.00 | 2.00 | 2.00 |
|  | 2E13HD | — | — | — | — | — | — | — |
|  | 2-Py | 10.00 | 10.00 | 10.00 | 10.00 | 10.00 | 10.00 | 10.00 |
|  | E1010 | 1.00 | 1.00 | 1.00 | 1.00 | 1.00 | 1.00 | 1.00 |
|  | TEA | 1.00 | 1.00 | 1.00 | 1.00 | 1.00 | 1.00 | 1.00 |
|  | Urea | 5.00 | 5.00 | 5.00 | 5.00 | 5.00 | 5.00 | 5.00 |
|  | BTA | 0.01 | 0.01 | 0.01 | 0.01 | 0.01 | 0.01 | 0.01 |
|  | EDTA | 0.02 | 0.02 | 0.02 | 0.02 | 0.02 | 0.02 | 0.02 |
|  | XL2 | 0.20 | 0.20 | 0.20 | 0.20 | 0.20 | 0.20 | 0.20 |
|  | ECTD3NEX | — | — | — | — | — | — | — |
|  | SAG30 | — | — | — | — | — | — | — |
|  | Water | 65.70 | 65.07 | 70.76 | 53.27 | 67.67 | 64.77 | 66.75 |
| Total |  | 100 | 100 | 100 | 100 | 102 | 100 | 101 |

TABLE 2

| | | Example | | | Comparative Example | | | | |
|---|---|---|---|---|---|---|---|---|---|
| | | 16 | 17 | 18 | 1 | 2 | 3 | 4 | 5 |
| Content [parts by mass] | AB172 | — | — | 4.00 | 10.00 | 10.00 | 10.00 | — | — |
| | AB194 | 10.00 | 10.00 | 4.00 | — | — | — | 10.00 | 10.00 |
| | Formula (1) | 0.04 | 0.40 | 0.20 | — | 0.01 | 10.00 | 0.01 | 10.00 |
| | Formula (2) | 0.01 | 0.10 | 0.05 | — | — | — | — | — |
| | Formula (3) | 0.01 | 0.10 | 0.05 | — | — | — | — | — |
| | Formula (4) | 0.01 | 0.10 | 0.05 | — | — | — | — | — |
| | Gly | 3.00 | 3.00 | 3.00 | 3.00 | 3.00 | 3.00 | 3.00 | 3.00 |
| | DEG | 1.00 | 1.00 | 1.00 | 1.00 | 1.00 | 1.00 | 1.00 | 1.00 |
| | TEG | 1.00 | 1.00 | 1.00 | 1.00 | 1.00 | 1.00 | 1.00 | 1.00 |
| | TEGmBE | 2.00 | 2.00 | 2.00 | 2.00 | 2.00 | 2.00 | 2.00 | 2.00 |
| | 2E13HD | — | — | — | — | — | — | — | — |
| | 2-Py | 10.00 | 10.00 | 10.00 | 10.00 | 10.00 | 10.00 | 10.00 | 10.00 |
| | E1010 | 1.00 | 1.00 | 1.00 | 1.00 | 1.00 | 1.00 | 1.00 | 1.00 |
| | TEA | 1.00 | 1.00 | 1.00 | 1.00 | 1.00 | 1.00 | 1.00 | 1.00 |
| | Urea | 5.00 | 5.00 | 5.00 | 5.00 | 5.00 | 5.00 | 5.00 | 5.00 |
| | BTA | 0.01 | 0.01 | 0.01 | 0.01 | 0.01 | 0.01 | 0.01 | 0.01 |
| | EDTA | 0.02 | 0.02 | 0.02 | 0.02 | 0.02 | 0.02 | 0.02 | 0.02 |
| | XL2 | 0.20 | 0.20 | 0.20 | 0.2 | 0.2 | 0.2 | 0.2 | 0.2 |
| | ECTD3NEX | — | — | — | — | — | — | — | — |
| | SAG30 | — | — | — | — | — | — | — | — |
| | Water | 65.70 | 65.07 | 67.07 | 65.77 | 65.76 | 55.76 | 65.76 | 55.77 |
| | Total | 100 | 100 | 100 | 100 | 100 | 100 | 100 | 100 |

[2] Evaluation

[2-1] Idle Running Test

The composition for aqueous ink jet of each of the examples and the comparative examples was filled in an ink cartridge of recoding apparatus PX-G930 (manufactured by Seiko Epson Corporation) serving as a printer, and in printing on A4-size OPP paper at a resolution of 720 dpi in a longitudinal direction and 720 dpi in a transverse direction, it was confirmed that the ink composition was ejected from all nozzles. Then, the head was reciprocated 20 times without ejection, and then the number of non-ejection nozzles was examined by a nozzle check pattern and evaluated according to the following criteria. The recording apparatus (printer) was operated in an environment of 35° C. and 35 RH %.

A: The number of missing nozzles was zero.
B: The number of missing nozzles was 1 or more and 5 or less.
C: The number of missing nozzles was 6 or more and 14 or less.
D: The number of missing nozzles was 15 or more and 29 or less.
E: The number of missing nozzles was 30 or more.

[2-2] Test of Allowing to Stand

The composition for aqueous ink jet of each of the examples and the comparative examples was filled in an ink cartridge of printing apparatus PX-G930 (manufactured by Seiko Epson Corporation) serving as a printer, and in printing on A4-size OPP paper at a resolution of 720 dpi in a longitudinal direction and 720 dpi in a transverse direction, it was confirmed that the ink composition was ejected from all nozzles. Then, the printer was allowed to stand for 6 months in an environment of a temperature of 25° C. and a relative humidity of 35%. After being allowed to stand, the composition was again ejected from all nozzles, and the number of times of cleaning required until printing equivalent to the initial printing was possible was measured. Based on the number of times of cleaning, clogging recovery was evaluated according to the following criteria.

A: Recovery was achieved by 0 to 1 time of cleaning.
B: Recovery was achieved by 2 to 3 times of cleaning.
C: Recovery was achieved by 4 to 6 times of cleaning.
D: Recovery was achieved by 7 to 9 times of cleaning.
E: Recovery was not achieved even by 9 times of cleaning.

These results are summarized in Table 3.

TABLE 3

| | Idle running test | Test of allowing to stand |
|---|---|---|
| Example 1 | A | A |
| Example 2 | B | B |
| Example 3 | A | A |
| Example 4 | A | A |
| Example 5 | B | B |
| Example 6 | A | A |
| Example 7 | A | A |
| Example 8 | A | A |
| Example 9 | A | A |
| Example 10 | A | A |
| Example 11 | C | B |
| Example 12 | B | C |
| Example 13 | A | A |
| Example 14 | B | B |
| Example 15 | A | A |
| Example 16 | A | A |
| Example 17 | B | B |
| Example 18 | A | A |
| Comparative Example 1 | E | D |
| Comparative Example 2 | D | C |
| Comparative Example 3 | C | D |
| Comparative Example 4 | D | C |
| Comparative Example 5 | C | D |

Table 3 indicates that the examples produce excellent results. Whereas, the comparative examples could not produce satisfactory results.

The invention claimed is:

1. A composition for an aqueous ink jet ink comprising:
a specific dye which is one or more coloring materials selected from the group consisting of C. I. Acid Black 172 and C. I. Acid Black 194; and
a specific aromatic compound which is at least one compound selected from the group consisting of a compound represented by formula (1) below, a compound represented by formula (2) below, and a compound represented by formula (3) below,
wherein the content of the specific aromatic compound relative to 100 parts by mass of the specific dye is 0.2 parts by mass or more and 50 parts by mass or less

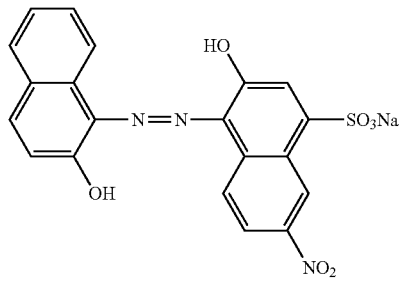

(1)

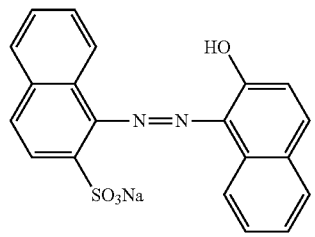

(2)

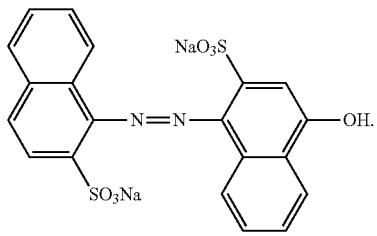

(3)

2. The composition for an aqueous ink jet ink according to claim 1, wherein the content of the specific aromatic compound in the composition for aqueous ink jet is 0.02% by mass or more and 5.0% by mass or less.

3. The composition for an aqueous ink jet ink according to claim 1, wherein the content of the specific dye in the composition for aqueous ink jet is 5.0% by mass or more and 15% by mass or less.

4. The composition for an aqueous ink jet according to claim 1, wherein the viscosity at 25° C. is 2 mPa·s or more and 30 mPa·s or less.

* * * * *